(12) United States Patent
Maruyama et al.

(10) Patent No.: US 10,688,199 B2
(45) Date of Patent: Jun. 23, 2020

(54) THERANOSTIC BUBBLE PREPARATION (TB), AND METHOD FOR USING SAME

(71) Applicant: TEIKYO UNIVERSITY, Tokyo (JP)

(72) Inventors: Kazuo Maruyama, Tokyo (JP); Ryo Suzuki, Tokyo (JP); Johan Mikael Unga, Tokyo (JP); Daiki Omata, Tokyo (JP); Yusuke Oda, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 34 days.

(21) Appl. No.: 15/579,140

(22) PCT Filed: Jun. 10, 2016

(86) PCT No.: PCT/JP2016/002810
§ 371 (c)(1),
(2) Date: Dec. 1, 2017

(87) PCT Pub. No.: WO2016/199430
PCT Pub. Date: Dec. 15, 2016

(65) Prior Publication Data
US 2018/0161462 A1 Jun. 14, 2018

(30) Foreign Application Priority Data
Jun. 10, 2015 (JP) .................... 2015-117793

(51) Int. Cl.
| | |
|---|---|
| A61K 49/22 | (2006.01) |
| A61K 31/02 | (2006.01) |
| A61K 47/69 | (2017.01) |
| A61P 35/00 | (2006.01) |
| A61K 9/00 | (2006.01) |
| A61K 9/19 | (2006.01) |
| A61K 47/24 | (2006.01) |
| A61K 47/36 | (2006.01) |
| A61K 47/42 | (2017.01) |

(52) U.S. Cl.
CPC .......... *A61K 49/223* (2013.01); *A61K 9/0009* (2013.01); *A61K 9/19* (2013.01); *A61K 31/02* (2013.01); *A61K 47/24* (2013.01); *A61K 47/36* (2013.01); *A61K 47/42* (2013.01); *A61K 47/6925* (2017.08); *A61P 35/00* (2018.01)

(58) Field of Classification Search
CPC .. A61K 31/02; A61K 49/223; A61K 47/6925; A61K 47/42; A61K 9/19; A61K 47/24; A61K 47/36; A61K 9/0009; A61P 35/00
See application file for complete search history.

(56) References Cited

U.S. PATENT DOCUMENTS

| | | | |
|---|---|---|---|
| 6,221,337 B1 * | 4/2001 | Dugstad ................ | A61K 49/22 424/9.52 |
| 2004/0265393 A1 | 12/2004 | Unger et al. | |
| 2005/0025710 A1 | 2/2005 | Schneider et al. | |
| 2005/0100963 A1 | 5/2005 | Sato et al. | |
| 2006/0037440 A1 * | 2/2006 | Kozak ................ | B23B 51/00 81/53.2 |
| 2007/0232913 A1 | 10/2007 | Lau et al. | |
| 2008/0139942 A1 * | 6/2008 | Gaud ................ | A61K 49/223 600/458 |
| 2009/0088636 A1 | 4/2009 | Lau et al. | |
| 2010/0158814 A1 | 6/2010 | Bussat et al. | |
| 2011/0059024 A1 | 3/2011 | Hirai et al. | |
| 2011/0236320 A1 * | 9/2011 | Schneider ............ | A61K 49/223 424/9.52 |
| 2012/0009243 A1 * | 1/2012 | Vikbjerg .............. | A61K 9/1271 424/450 |
| 2013/0022550 A1 * | 1/2013 | Unger .................. | A61K 49/223 424/9.52 |
| 2014/0328767 A1 * | 11/2014 | Wang .................. | B01F 11/0266 424/9.52 |

FOREIGN PATENT DOCUMENTS

| | | |
|---|---|---|
| JP | 2001-205061 A | 7/2001 |
| JP | 2003-048826 A | 2/2003 |
| JP | 2007-516957 A | 6/2007 |
| JP | 2009-161549 A | 7/2009 |
| JP | 2009-533188 A | 9/2009 |
| JP | 2010-512400 A | 4/2010 |
| JP | 2011-057591 A | 3/2011 |
| WO | WO 2014/030601 A1 | 2/2014 |

OTHER PUBLICATIONS

Fan et al., 2012 IEEE International Ultrasonics Symposium Proceedings, p. 2274-2277. (Year: 2012).*
Kurosaki et al., J. Controlled Release, 2014, 176, p. 24-34 (Year: 2014).*
International Preliminary Examining Authority (IPEA), Written Opinion, including Applicant's Response and Amended Claims to ISA's Written Opinion, for International Application No. PCT/JP2016/002810, dated May 23, 2017, 22 pages, Japan Patent Office, Japan.
International Preliminary Examining Authority, International Preliminary Report on Patentability, including Applicant's Response to IPEA's Written Opinion, for International Application No. PCT/JP2016/002810, dated Jul. 25, 2017, 18 pages, Japan Patent Office.
International Searching Authority (ISA), International Search Report (ISR) and Written Opinion for International Application No. PCT/JP2016/002810, dated Jul. 19, 2016, 12 pages, Japan Patent Office, Japan.

(Continued)

*Primary Examiner* — Michael G. Hartley
*Assistant Examiner* — Leah H Schlientz
(74) *Attorney, Agent, or Firm* — Alston & Bird LLP (57) ABSTRACT

Provided is a theranostic bubble preparation which makes it possible to diagnose and treat a tissue of interest by the irradiation with ultrasound such as diagnostic ultrasound and low-intensity therapeutic ultrasound. The theranostic bubble preparation comprises: a coating film comprising a lipid; and a gas enclosed in an inner cavity formed in the coating film. The coating film comprises an anionic lipid made from distearoylphosphatidylcholine (DSPC), distearoylphosphatidylglycerol (DSPG) and 1,2-distearoyl-sn-glycero-3-phosphoethanolamine-N-[methoxy(polyethylene glycol)-2000] (DSPE-PEG$_{2000}$). The gas and the mixed gas comprises perfluoropropane or perfluorobutane.

9 Claims, 10 Drawing Sheets

(56) References Cited

OTHER PUBLICATIONS

Javadi, M., et al., "Encapsulating nanoemulsions inside eLiposomes for ultrasonic drug delivery", Langmuir, Sep. 18, 2012 (Web), vol. 28, pp. 14720-14729, American Chemical Society, USA.

Lawrie, A., et al., "Microbubble-enhanced ultrasound for vascular gene delivery", Gene Therapy, 2000, pp. 2023-2027, vol. 7, Macmillan Publishers Ltd., UK.

Mitragotri, S., "Healing sound: the use of ultrasound in drug delivery and other therapeutic applications", Nature Reviews, Drug Discovery, Perspectives, Mar. 2005, pp. 255-259, vol. 4, Nature Publishing Company, UK.

Negishi, Y., et al., "Gene and nucleic acid delivery using ultrasound-responsive Bubble liposomes: toward development of theranostics agents", Drug Delivery System, 2014, pp. 285-293, vol. 29, J-Stage, Japan.

Sax N. et al., "Optimization of Acoustic Liposomes for Improved in Vitro and in Vivo Stability", Pharmaceutical Research, 2013, pp. 218-224, vol. 30, Springer, USA.

\* cited by examiner

THERANOSTIC BUBBLE PREPARATION (TB), AND METHOD FOR USING SAME

CROSS REFERENCE TO RELATED APPLICATIONS

This application is a national stage application, filed under 35 U.S.C. § 371, of International Application No. PCT/JP2016/002810, filed Jun. 10, 2016, which claims priority to Japanese Application No. 2015-117793, filed Jun. 10, 2015, the contents of both of which as are hereby incorporated by reference in their entirety.

BACKGROUND

Technical Field

The present invention relates to a theranostic bubble (TB) preparation which enables diagnostics and therapeutics for a tissue of interest, and a method for using the theranostic bubble preparation.

Description of Related Art

An ultrasound contrast medium is a suspension containing microbubbles. Examples of the main ultrasound contrast media used in Japan include Levovist® and Sonazoid®. Levovist is used in diagnostic cardiovascular angiography. Sonazoid is used for diagnosis of hepatoma based on Kupffer cell contrast imaging, and for diagnosis of mammary gland tumor. The microbubbles of Levovist each have a coating of galactose that is a carbohydrate, and encapsulate air thereinside. The microbubbles of Sonazoid each have a coating of phosphatidylserine sodium that is a phospholipid, and encapsulate perflubutane thereinside.

However, these ultrasound contrast media have no therapeutic function. Therefore, clinical professionals have created a demand for the contrast media to have an extended functionality. In addition, theranostics which is a combination of diagnosis and therapeutics has received attention recently. The theranostics refers to a system for carrying out diagnosis and treatment at the same time. Also in the field of DDS, attention has been focused on the development of high-functionality nanocarriers usable as theranostic preparations.

Ultrasound diagnosis, which is one of the diagnostic methods that have been clinically applied, is advantageous because it is noninvasive, simple, relatively inexpensive, and capable of providing diagnostic imaging on a real-time basis. Due to these advantages, diagnostic methods using ultrasound diagnosis apparatuses have been employed as indispensable methods in various clinical areas. The physical energy of ultrasound has already been used in clinical sites, not only for diagnosis, but also for treatment.

For example, some reports have been made on a method for delivering a drug or genes to the inside of cells by using in combination microbubbles that are in clinical use as an ultrasound contrast medium for, e.g., angiography, and ultrasonic irradiation (Non-Patent Documents 1 and 2). According to this method, collapse of microbubbles (cavitation) caused by the extracorporeal ultrasound irradiation is temporally and spatially controlled, thereby enabling efficient introduction of a drug or genes only to a region subjected to the ultrasound irradiation. It is expected that this method will facilitate specific introduction of genes and nucleic acid to an organ or a tissue. It has been reported that in vitro and in vivo gene transfer has been carried out in various tissues by this method.

High intensity focused ultrasound (HIFU) treatment is becoming common as a method for destroying cancer cells without performing a surgical operation. In the HIFU treatment, high intensity ultrasound (e.g., having an energy intensity ranging from 3000 W/cm$^2$ to 5000 W/cm$^2$) is extracorporeally focused on a point of a cancer tissue within a body so that the cancer tissue is cauterized and necrosed by the thermal energy (a thermal action) and cavitation (a nonthermal action) (Patent Document 1). This effect is provided by the destruction and cauterization of cancer tissue caused by the thermal energy heating the focus region to 80° C. to 90° C. approximately.

However, a single operation of the HIFU treatment can cauterize an area of, for example, 3 mm×3 mm×10 mm. It is therefore necessary to repeat the irradiation while shifting the focus. In the HIFU treatment, placing the focus on a point outside a target area creates a great danger. Therefore, the HIFU treatment is carried out under the guidance of MRI or an ultrasound image. Moreover, since the skin and a surrounding region are heated to a high temperature, the HIFU treatment constantly requires precise control and cooling time to be ensured. As a result, the HIFU treatment usually needs two to four hours for implementation.

As can be seen, the HIFU treatment is an ideal noninvasive treatment. On the other hand, if a therapeutically functional bubble preparation can be introduced to a cancer tissue, cancer treatment can be carried out by causing cavitation only in the region where the bubbles are present, using low intensity ultrasound which is approximately $\frac{1}{100}$ to $\frac{1}{500}$ as high as the ultrasonic used in the HIFU treatment.

Patent Document 1: Japanese Unexamined Patent Publication (Japanese Translation of PCT Application) No. 2009-533188

Non-Patent Document 1: Mitragotri S, Healing sound: the use of ultrasound in drug delivery and other therapeutic applications. Nature Rev. Drug Discov. 2005; 4: 255-259.

Non-Patent Document 2: Lawrie A, Brisken A F, Francis S E, Cumberland D C, Crossman D C, Newman C M, Microbubble-enhanced ultrasound for vascular gene delivery. Gene Ther., 2000; 7: 2023-2027.

BRIEF SUMMARY

In view of the foregoing background, it is therefore an object of the present invention to provide a theranostic bubble preparation which makes it possible to diagnose and treat a tissue of interest by irradiation with low intensity ultrasound, and a method for using the theranostic bubble preparation.

A theranostic bubble (TB) preparation of the present invention includes bubbles and enables diagnostics and therapeutics for a tissue of interest through an action of low intensity therapeutic ultrasound. The bubbles each include a coating of lipid and a gas encapsulated in an inner cavity defined by the coating. The lipid forming the coating is an anionic lipid including distearoylphosphatidylcholine (DSPC), distearoylphosphatidylglycerol (DSPG), and 1,2-distearoyl-sn-glycero-3-phosphoethanolamine-N-[methoxy(polyethyleneglycol)] (DSPE-PEG) at a molar ratio of 22-60:30-68:4-12. The gas includes at least one of perfluoropropane, perfluorobutane, perfluoropentane, or perfluorohexane, or a mixed gas thereof.

A method for using the theranostic bubble (TB) preparation of the present invention includes: introducing, to a tissue of interest, a suspension including water for injection and the theranostic bubble preparation of the present invention suspended in the water for injection, subjecting the tissue of interest to an action of diagnostic ultrasound having a first frequency to carry out diagnostics based on imaging of the tissue of interest, and subjecting the tissue of interest to an action of the low intensity therapeutic ultrasound having a second frequency to carry out therapeutics for the tissue of interest by a cavitation phenomenon.

Unlike the microbubbles of the known art, the bubbles of the theranostic bubble preparation of the present invention are not destroyed by irradiation with diagnostic ultrasound, and capable of continuing sympathetic vibration and resonance for a long time, thereby enabling long-duration and continuous ultrasonic imaging. The present invention makes it possible to diagnose and treat a tissue of interest through irradiation with low intensity therapeutic ultrasound. Using such low intensity focused ultrasound (LOFU) does not increase the temperature of the focus region, and thus enhances safety. It is thus expected that an ultrasound theranostic system will be established for safer early diagnosis and treatment of thrombi, and minimally invasive treatment of compromised brain function, renal diseases, and so on.

DETAILED DESCRIPTION OF VARIOUS EMBODIMENTS

Embodiments of the present invention will now be described specifically with reference to the attached drawings. Note that the following embodiments are described for better understanding of the principles of the present invention, and that the scope of the present invention is not limited to the following embodiments. Other embodiments corresponding to the following embodiments of which a configuration is appropriately replaced by the skilled person are also included in the scope of the present invention.

1. <Theranostic Bubble Preparation>

A theranostic bubble preparation according to this embodiment contains bubbles each including a coating of lipid, and a gas encapsulated in an inner cavity defined by the coating.

The lipid is an anionic lipid including distearoylphosphatidylcholine (DSPC), distearoylphosphatidylglycerol (DSPG), and 1,2-distearoyl-sn-glycero-3-phosphoethanolamine-N-[methoxy(polyethyleneglycol)] (DSPE-PEG) at a molar ratio of 22-60:30-68:4-12.

The gas is a perfluorohydrocarbon gas. Specifically, the gas includes at least one of perfluoropropane, perfluoroisobutane, or perfluoronormalbutane, or a mixed gas of the foregoing substances. A particularly preferable perfluorohydrocarbon gas is perfluoropropane because perfluoropropane is a medical gas commercially available in Japan. Note that the gas may contain perfluorohydrocarbon other than these. Specifically, examples of such perfluorohydrocarbon include perfluoromethane, perfluoroethane, perfluoroisooctane, perfluoronormaloctane, and sulfur hexafluoride. The gas filled has a pressure ranging from 0.1 MPa to 1.0 MPa, for example.

The theranostic bubble preparation of the present invention is comprised of microbubbles each including phospholipid and PEG-lipid and a hydrophobic fluorocarbon gas encapsulated by the phospholipid and PEG-lipid. The microbubbles have a diameter ranging from 500 nm to 5 μm and are present as bubbles in a liquid. The diameter of the bubbles of the theranostic bubble preparation is measured by, for example, dynamic light scattering.

Including DSPC, DSPG, and DSPE-PEG at a molar ratio of 22-60:30-68:4-12, the coating has enhanced capability of retaining perfluorohydrocarbon, and continuously exhibits sympathetic vibration and resonance without being destroyed by irradiation with diagnostic ultrasound. These characteristics of the coating enable long-duration and continuous ultrasonic imaging.

Among DSPC, DSPG, and DSPE-PEG forming the coating, DSPE may be replaced with the following phospholipids, for example: phosphatidylethanolamine such as dimyristoyl-phosphatidylethanolamine (DMPE), dipalmitoylphosphatidylethanolamine (DPPE), dioleylphosphatidylethanolamine (DOPE), distearoylphosphatidylethanolamine (DSPE), diarachidoylphosphatidylethanolamine (DAPE), or dilinoleoylphosphatidylethanolamine (DLPE); phosphatidylcholine such as dilauroyl-phosphatidylcholine (DLPC), dimyristoylphosphatidylcholine (DMPC), dipalmitoyl-phosphatidylcholine (DPPC), diarachidoyl-phosphatidylcholine (DAPC), and dioleyl-phosphatidylcholine (DOPC); phosphatidylserine such as dimyristoylphosphatidylserine (DMPS), diarachidoylphosphatidylserine (DAPS), dipalmitoylphosphatidylserine (DPPS), distearoylphosphatidylserine (DSPS), and dioleylphosphatidylserine (DOPS); phosphatidic acid derivatives such as dipalmitoyl phosphatidic acid (DPPA), dimyristoyl phosphatidic acid (DMPA), distearoyl phosphatidic acid (DSPA), diarachidoyl phosphatidic acid (DAPA), and an alkali metal salt thereof; phosphatidylglycerol such as dimyristoylphosphatidylglycerol (DMPG) and an alkali metal salt thereof, dipalmitoylphosphatidylglycerol (DPPG) and an alkali metal salt thereof, distearoylphosphatidylglycerol (DSPG) and an alkali metal salt thereof, and dioleyl-phosphatidylglycerol (DOPG); and phosphatidylinositol such as dilauroylphosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), and dioleylphosphatidylinositol (DOPI).

Further, among DSPC, DSPG, and DSPE-PEG forming the coating, DSPE-PEG may be replaced with, for example, stearyl PEG, palmitoyl PEG, and oleic acid PEG, myristyl PEG, and lauroyl PEG.

PEG has a molecular weight ranging from 500 to 12000, for example. DSPE-PEG is preferably DSPE-PEG$_{2000}$, DSPE-PEG$_{3000}$, or DSPE-PEG$_{5000}$, and particularly preferably DSPE-PEG$_{2000}$.

The coating may contain, in addition to DSPC, DSPG, and DSPE-PEG, the following phospholipids: phosphatidylcholine such as dimyristoylphosphatidylcholine (DMPC), dilauroylphosphatidylcholine (DLPC), dipalmitoylphosphatidylcholine (DPPC), dioleoylphosphatidylcholine (DOPC), and dilinoleoylphosphatidylcholine; phosphatidylglycerol such as dilauroylphosphatidylglycerol (DLPG), dimyristoylphosphatidylglycerol (DWG), dipalmitoylphosphatidylglycerol (DPPG), dioleoylphosphatidylglycerol (DOPG), and dilinoleoylphosphatidylglycerol; phosphatidylethanolamine such as dilauroylphosphatidylethanolamine (DLPE), dimyristoylphosphatidylethanolamine (DMPE), dipalmitoylphosphatidylethanolamine (DPPE), distearoylphosphatidylethanolamine (DSPE), dioleoylphosphatidylethanolamine (DOPE), and dilinoleoylphosphatidylethanolamine; and phosphatidylcholine such as dilauroylphosphatidylserine (DLPS), dimyristoylphosphatidylserine (DMPS), dipalmitoylphosphatidylserine (DPPS), distearoylphosphatidylserine (DSPS), dioleoylphosphatidylserine (DOPS), and dilinoleoylphosphatidylserine.

Moreover, the coating may contain, in addition to the phospholipids described above, a glyceroglycolipid or a sphingoglycolipid, for example. Examples of the glyceroglycolipid include sulfoxy ribosylglyceride, diglycosyl diglyceride, digalactosyl diglyceride, galactosyl diglyceride, and glycosyl diglyceride. Examples of the sphingoglycolipid include galactosyl cerebroside, lactosyl cerebroside, and ganglioside.

Ligands for a target cell, a target tissue, and a target focus may be modified on a lipid surface of the coating. Examples of the ligands include a ligand for thrombus such as arginine-glycine-aspartic acid (RGD) sequence peptide and sigma protein, and a ligand for cancer cell such as transferrin, folic acid, hyaluronic acid, galactose, or mannose. In addition, monoclonal and polyclonal antibodies can also be used as the ligands. Preferably, the ligand is RGD peptide, which has the function of specifically binding to a cell adhesion factor existing on a particular cell or a thrombus. Therefore, modification of the RGD peptide on the lipid surface of the coating makes it further easy to visualize the thrombus.

To achieve the modification of the ligand on the lipid surface of the coating, the coating preferably includes DSPC, DSPG, and a DSPE-PEG derivative. Preferably, the DSPE-PEG derivative is preferably DSPE-PEG-Maleimide (MAL), DSPE-PEG-Carboxylic Acid (COOH), DSPE-PEG-N-Hydroxysuccinimide (NHS), or DSPE-PEG-NH$_2$, for example.

Other substances may be added to the coating as necessary. For example, the coating may include, as a coating stabilizing agent, sitosterol, cholesterol, dihydrocholesterol, cholesterol ester, phytosterol, stigmasterol, campesterol, cholestanol, lanosterol, 1-O-sterolglucoside, 1-O-sterolmaltoside, and a mixture thereof.

Further, the theranostic bubble preparation of the present invention can be prepared such that each coating encapsulates a drug thereinside, or absorbs a drug onto the inner surface thereof. It is preferable, for example, that the coating encapsulates or absorbs a drug which is desired to be kept at a certain blood concentration for a long period of time, or which needs to be administered in a manner intended to target a particular affected region or cell. Examples of the drug include, but are not limited to, an anticancer agent, an antibiotic, an antiasthmatic, an antithrombotic, an antiprotozoal, an immunopotentiator, a peptide drug, and an antiviral agent.

Examples of the anticancer agent include, but are not limited to, doxorubicin, cisplatin, mitomycin, bleomycin, 5-fluorouracil, methotrexate, nitrogen mustards, busulfan, oxaliplatin, taxol, and camptothecin. Examples of the antibiotic include sulfazen, gentamicin, and streptomycin. Examples of the antiasthmatic include theophylline. Examples of the antithrombotic include tPA, heparin, low-molecular-weight heparin, urokinase, thrombomodulin, and streptokinase. Examples of the antiprotozoal include meglumine antimoniate. Examples of the immunopotentiator include muramyl peptides. Examples of the peptide drug include natural or recombinant α, β, γ-interferons, interleukin, and superoxide dismutase. Examples of other drugs which may be encapsulated in or absorbed onto the coating include anti-arteriosclerosis agents such as prostaglandins, as well as NF-kappa B and decoy for arterial occlusive disease and Burger's disease.

Moreover, each coating of the theranostic bubble preparation can encapsulate thereinside or absorb onto the inner surface thereof, not only a drug, but also genes. Examples of the genes include DNA, RNA, antisense RNA, siRNA, decoy, and therapeutic oligonucleotide.

2. <Production Method of Theranostic Bubble Preparation>

Figure 1:
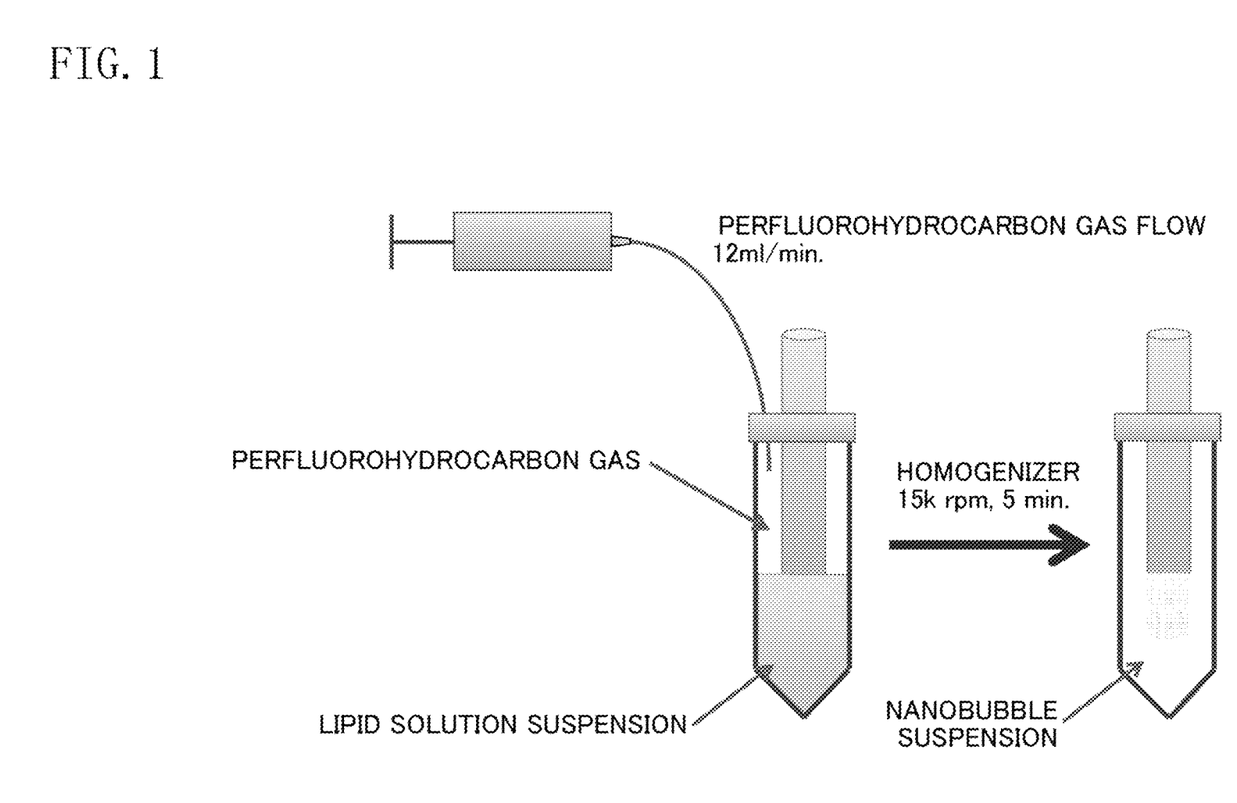
FIG. 1 shows a process for producing a theranostic bubble preparation of the present invention.

As shown in FIG. 1, the theranostic bubble preparation of the present invention can be produced in the following way: A lipid solution is brought into contact with perfluorohydrocarbon gas while being agitated in a manner forming a suspension. Thereafter, an organic phase is emulsified into an aqueous phase using a homogenizer (at 15000 rpm, for 5 minutes), thereby producing a nanobubble suspension, i.e., the theranostic bubble preparation.

Alternatively, the theranostic bubble preparation of the present invention can be prepared not only with the homogenizer, but also by shaking. For example, a solution containing liposomes at a predetermined ratio is put into a vial, and then is shaken with a vial shaker. The nanobubble suspension can also be prepared in this way.

3. <Freeze-Dried Powder>

The present invention also provides a freeze-dried powder. The freeze-dried powder is produced by freeze-drying a suspension including a carbohydrate solution of trehalose or sucrose and the theranostic bubble preparation of the present invention suspended in the carbohydrate solution.

For the freeze-drying, the suspension may contain a freeze-drying additive for cryoprotection and/or dispersion protection. Examples of the freeze-drying additive include an amino acid such as glycine; a saccharide such as mannitol, maltose, glucose, lactose, inulin, sucrose, trehalose, or cyclodextrin; a polysaccharide such as dextran or chitosan; or polyoxy alkylene glycol such as polyethylene glycol.

The freeze-dried powder may be stored for a period as long as three months or more. The freeze-dried powder is reconstituted with water for injection and the perfluorohydrocarbon gas above described, such as perfluoropropane.

4. <Method for Using Theranostic Bubble (TB) Preparation>

The theranostic bubble preparation of the present invention is used in the following way. A suspension including the theranostic bubble preparation of the present invention suspended in water for injection is introduced to a tissue of interest. Examples of the tissue of interest include, but are not limited to, a cancer tissue.

Next, the tissue of interest is subjected to the action of a diagnostic ultrasound having a first frequency, so that the tissue of interest is diagnosed based on imaging of the tissue of interest. The first frequency ranges from 3 MHz to 20 MHz, for example. The action of the first frequency causes a microstreaming phenomenon. Specifically, due to the acoustic pressure strength of the ultrasound, the nanobubbles vibrate locally while expanding and contracting repeatedly.

Next, the tissue of interest is subjected to the action of a low intensity ultrasound having a second frequency, so that the tissue of interest is treated by a cavitation phenomenon. The second frequency ranges from 0.5 MHz to 3.0 MHz, for example. The cavitation phenomenon refers to a phenomenon in which the nanobubbles release a large pressure upon collapsing, and consequently a jet flow occurs.

Subjecting the tissue of interest to the action of the diagnostic ultrasound having the first frequency enables imaging of the tissue of interest. The fact that the imaging is made possible means that irradiating the subject region with the low intensity ultrasound having the second frequency or a LOFU enables the treatment by the cavitation phenomenon. The irradiation of the low intensity ultrasound or LOFU alone does not increase the temperature of the focus region. Thus, a highly safe and minimally invasive treatment can be carried out.

EXAMPLES

Example 1. <Production of Theranostic Bubble Preparation>

An anionic lipid solution containing DSPC, DSPG, and DSPE-PEG$_{2000}$-OMe at a molar ratio of 22:68:10 was brought into contact with perfluoropropane gas (at a gas flowrate of 12 ml/min.) while being agitated in a manner forming a suspension. Thereafter, the gas was emulsified with a homogenizer (at 15000 rpm, for 5 minutes), thereby preparing a bubble suspension.

Next, other bubble suspensions were prepared in the same manner except that the molar ratio of the DSPC, DSPG, and DSPE-PEG$_{2000}$-OMe in the anionic solution was changed as indicated below.

DSPC:DSPG:DSPE-PEG$_{2000}$-OMe=30:60:10
DSPC:DSPG:DSPE-PEG$_{2000}$-OMe=36:54:10
DSPC:DSPG:DSPE-PEG$_{2000}$-OMe=45:45:10
DSPC:DSPG:DSPE-PEG$_{2000}$-OMe=54:36:10
DSPC:DSPG:DSPE-PEG$_{2000}$-OMe=60:30:10

Further, bubble suspensions of comparative examples were prepared in the same manner except that the molar ratio of the DSPC, DSPG, and DSPE-PEG$_{2000}$-OMe in the anionic solution was changed as indicated below.

DSPC:DSPG:DSPE-PEG$_{2000}$-OMe=0:90:10
DSPC:DSPG:DSPE-PEG$_{2000}$-OMe=90:0:10

Figure 2:
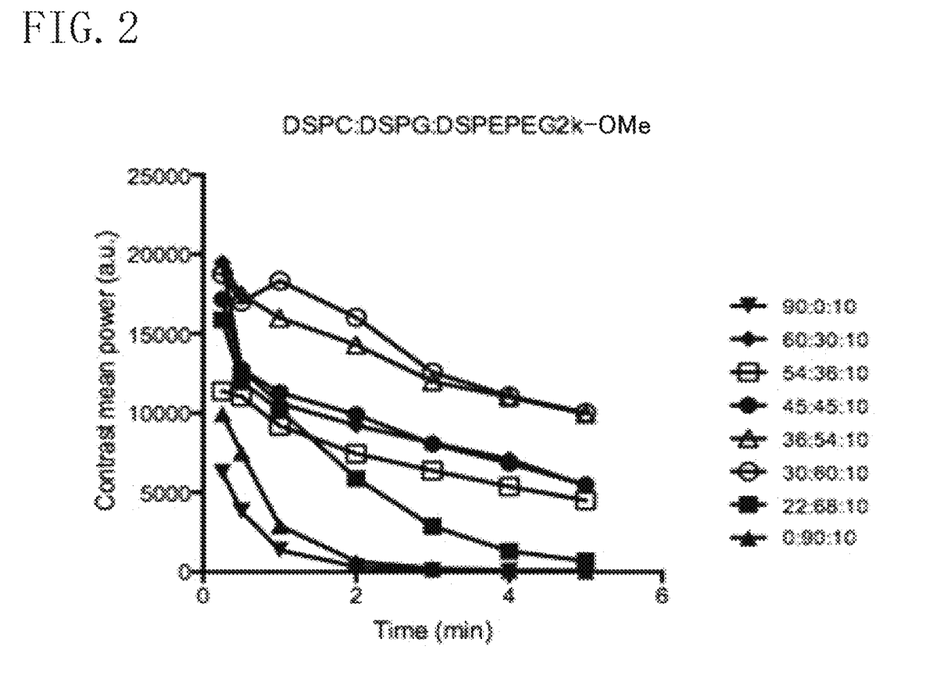
FIG. 2 shows durability of the bubble preparations including coatings having different constituent ratios.

In this manner, different bubble preparations of which the coatings had different constituent ratios were prepared. FIG. 2 shows durability of the nanobubbles of which the coatings had different constituent ratios. The bubbles need to be stable and capable of remaining in a blood vessel and a tumor. As shown in FIG. 2, even after the lapse of time, the bubble preparations of the present invention exhibited significantly higher capability of remaining than the bubble preparations of the comparative examples.

Example 2. <Continuous Imaging of Tumor-Bearing Mice>

Next, tumor-bearing mice were irradiated with diagnostic ultrasound to observe continuous oscillation possibility and to capture images of bloodstream.

A bubble preparation including nanobubbles was prepared in the following way: An anionic lipid solution containing DSPC, DSPG, and DSPE-PEG$_{2000}$-OMe at a molar ratio of 22:68:10 was brought into contact with perfluoropropane gas while being agitated in a manner forming a suspension. Thereafter, an organic phase was emulsified into an aqueous phase with a homogenizer (at 15000 rpm, for 5 minutes). Next, another bubble preparation was prepared in the same manner as described above except that perfluorobutane gas was used.

Ultrasound imaging was performed using a diagnostic ultrasound apparatus to see whether the nanobubbles reached tumor regions. As the diagnostic ultrasound apparatus, LOGIQ E9 (product of GE Healthcare) was used.

Figure 3:
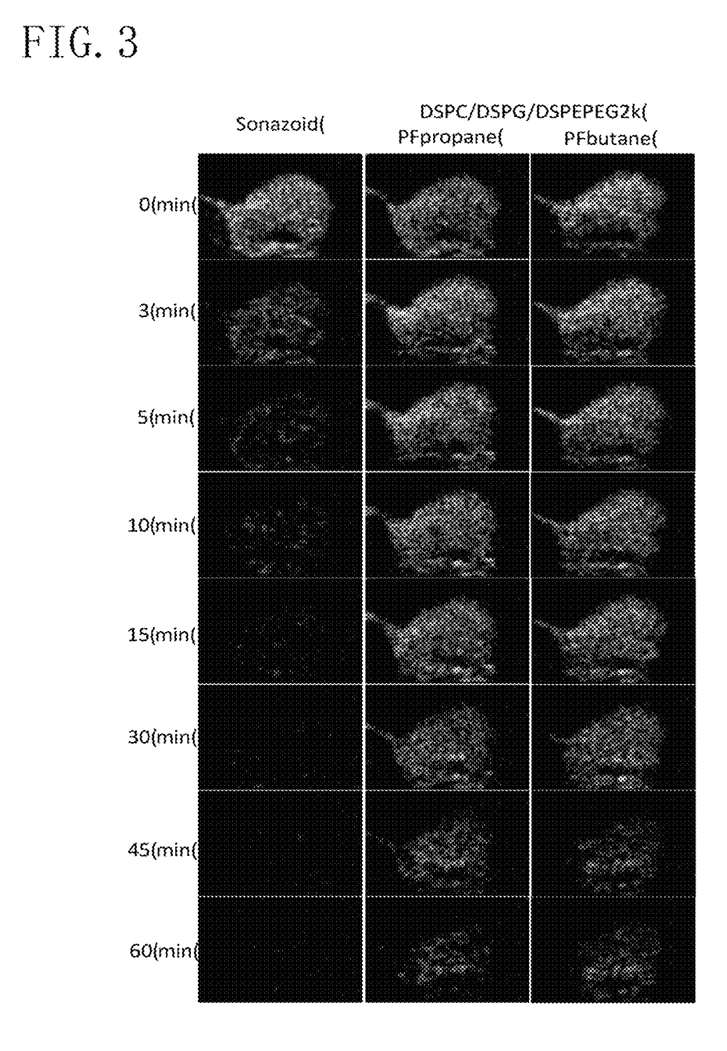
FIG. 3 shows the ultrasound images of tumor regions, captured with the passage of time, the tumor regions respectively administered with Sonazoid (comparative example), a bubble preparation with perfluoropropane gas encapsulated therein, and a bubble preparation with perfluorobutane gas encapsulated therein.

FIG. 3 shows the ultrasound images of the tumor regions, to which Sonazoid (comparative example), the bubble preparation with perfluoropropane gas encapsulated therein, and the bubble preparation with perfluorobutane gas encapsulated therein were administered respectively. The ultrasound images were captured with the passage of time. As shown in FIG. 3, the tumor regions administered with the bubble preparations of this example demonstrated stronger echo signals than the tumor region administered with the bubble preparation of the comparative example. It has been thus confirmed that the bubble preparation of the present invention is capable of stably reaching a target region. In addition, it was observed that the bubble preparations of this example emitted strong echo signals even after a lapse of time.

Figure 4:
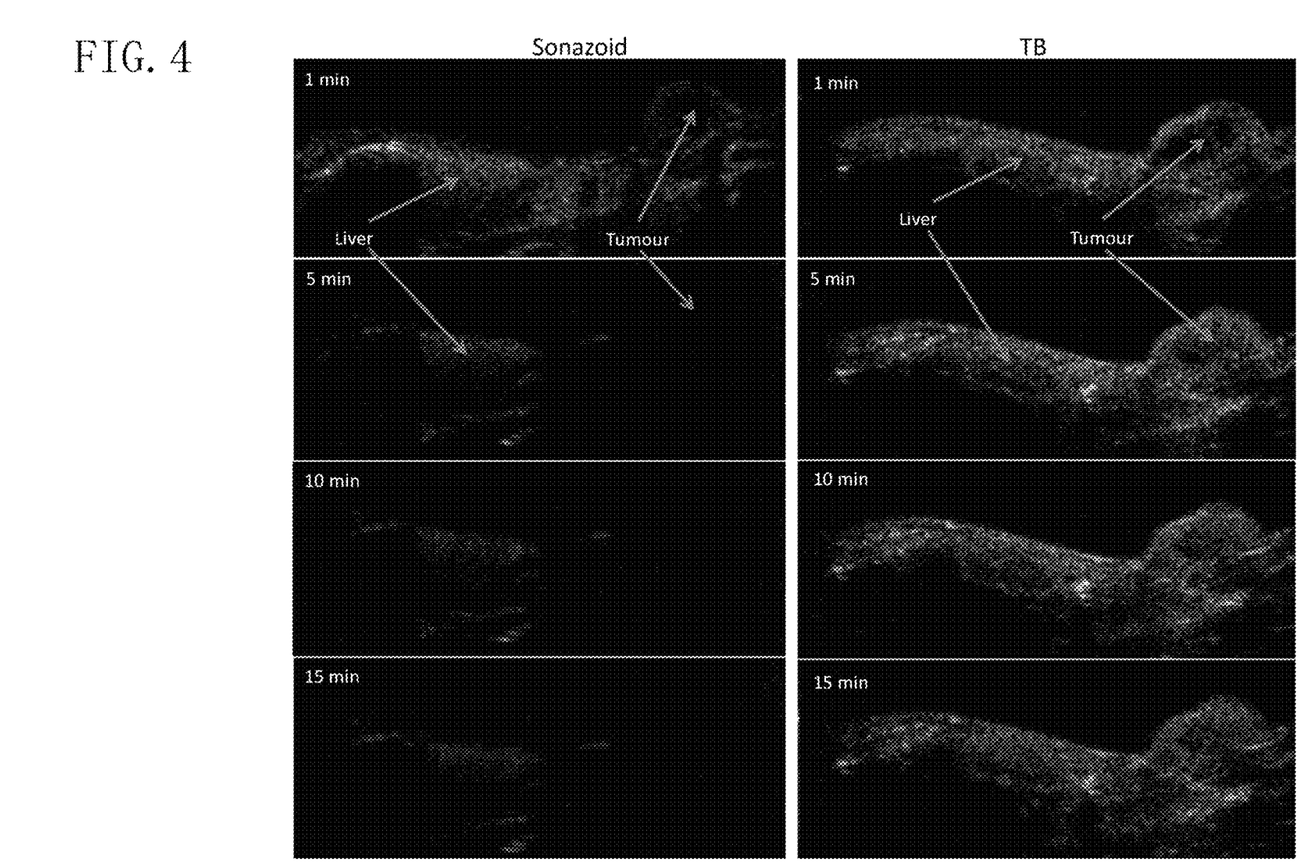
FIG. 4 shows enlarged ultrasound images of tumor regions respectively administered with Sonazoid (comparative example) and a bubble preparation with perfluoropropane gas encapsulated therein.

FIG. 4 shows enlarged ultrasound images of tumor regions, to which Sonazoid (comparative example) and the bubble preparation with perfluoropropane gas encapsulated therein were administered respectively. As shown in FIG. 4, the tumor region administered with the bubble preparation of this example demonstrated stronger echo signals than the tumor region administered with the bubble preparation of the comparative example.

Example 3. <Gene Introduction with Ultrasound>

Figure 5:
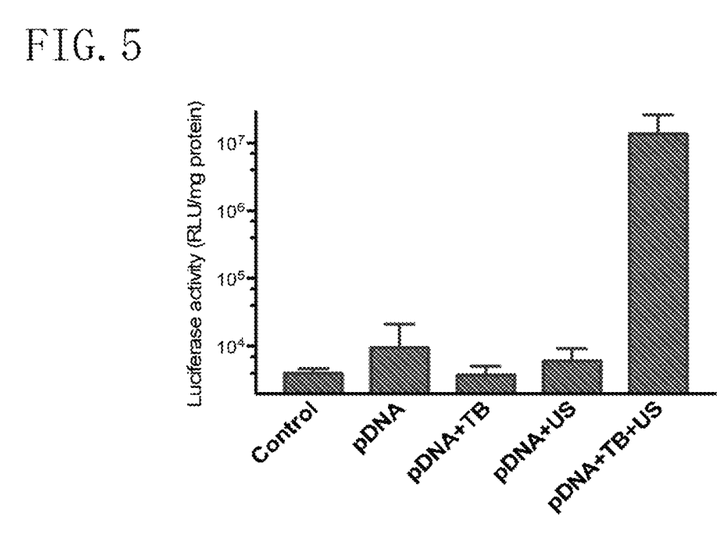
FIG. 5 shows increases in luciferase activity exhibited in in vivo livers to which luciferase genes were introduced.
Figure 6:
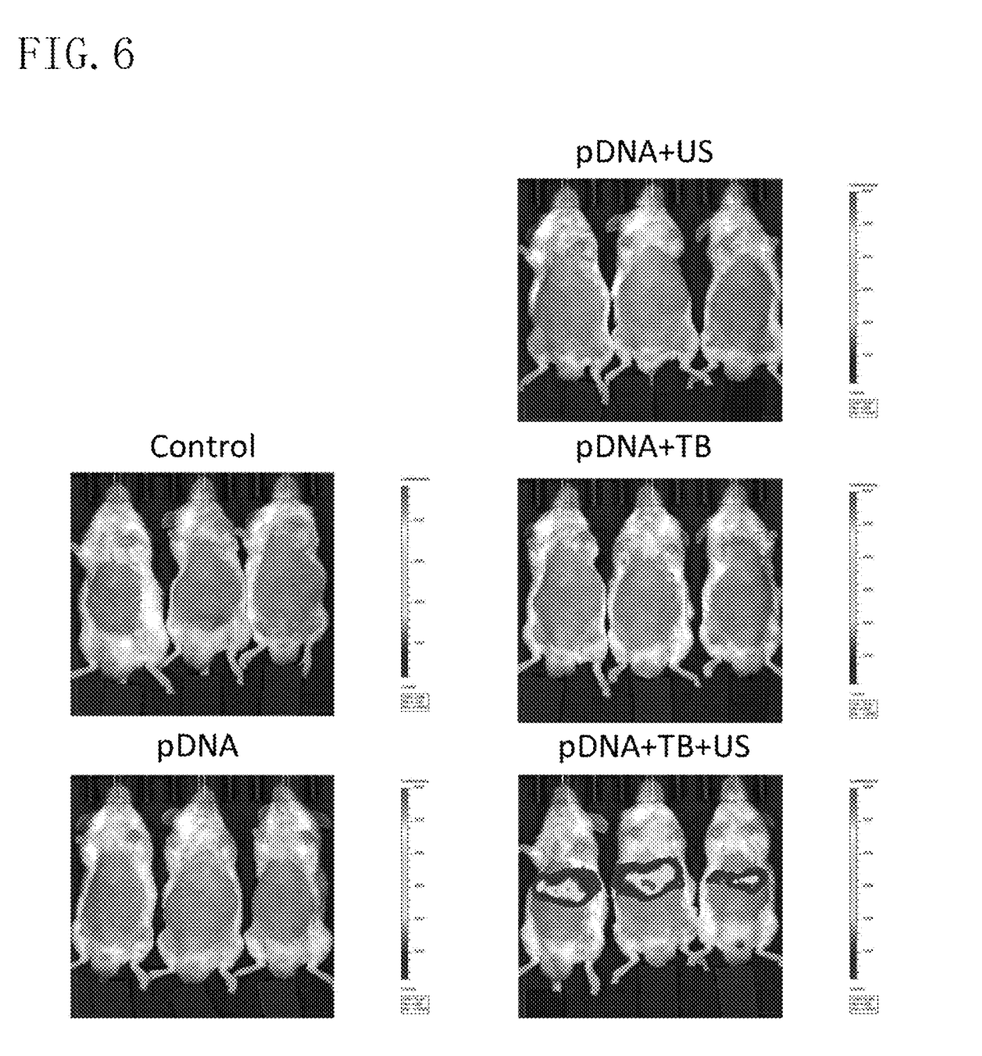
FIG. 6 shows results of luminescence imaging exhibited in in vivo livers to which luciferase genes were introduced.

Next, an evaluation was made on the function of a gene introduction system using in combination the bubble preparation (TB) with perfluoropropane gas encapsulated therein and low intensity ultrasound irradiation. In an in vivo experiment, the bubble preparation with perfluoropropane gas encapsulated therein (50 nmol) of this example and pDNA (100 μg) coded with a reporter gene (luciferase) were administered together to mice from its tail vein. Immediately after the administration, a liver portion was percutaneously irradiated with therapeutic ultrasound (US) (1 MHz, 50% duty, 1 W/cm$^2$, 60 secs.) using a sonitron probe (12 nm). FIG. 5 shows increases in luciferase activity. For in vivo luminescence imaging, following administration of luciferin substrate (15 mg/mL, 200 μL) to mice under isoflurane anesthesia, the luminescence was detected and quantified using IVIS imaging system. FIG. 6 shows the results of the in vivo luminescence imaging. As shown in FIGS. 5 and 6, the expression of luciferase was observed only at the livers irradiated with the therapeutic ultrasound.

Figure 7:
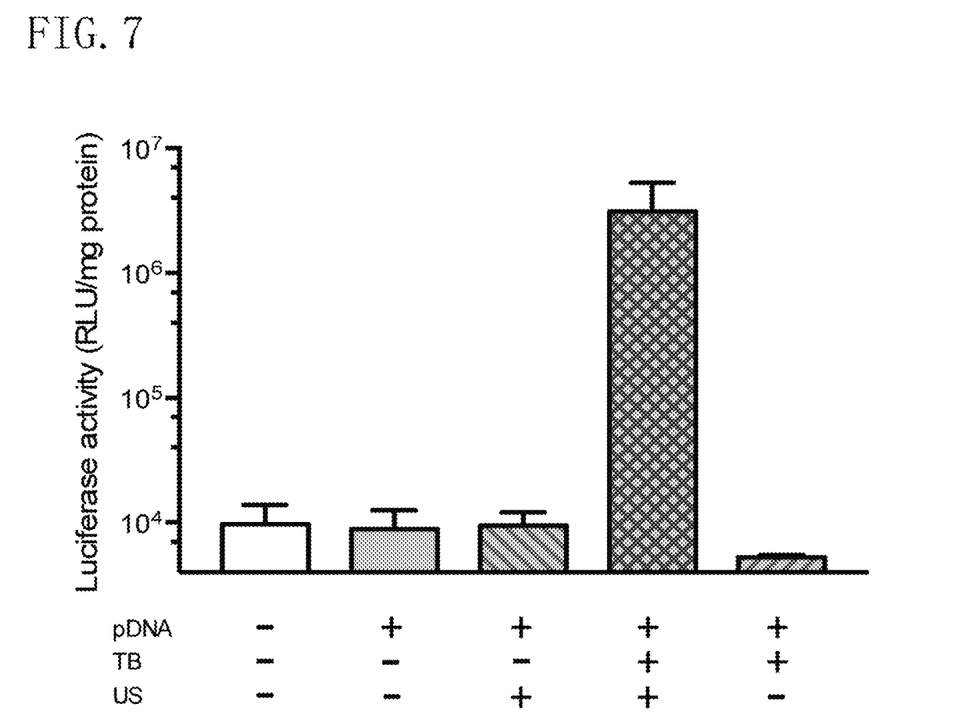
FIG. 7 shows increases in luciferase activity exhibited in in vitro colon26 cultured cells to which luciferase genes were introduced.

In an in vitro experiment, the bubble preparation with perfluoropropane gas encapsulated therein (5 nmol/sample) of this example and pDNA (5 µg/sample) coded with a reporter gene (luciferase) were together added to Colon 26 culture cell liquid. The liquid was then irradiated with therapeutic ultrasound (2 MHz, 50% duty, 2 W/cm$^2$, 60 secs.). As shown in FIG. 7, only the sample to which the bubble preparation with perfluoropropane gas encapsulated therein was added and which was irradiated with the therapeutic ultrasound demonstrated notable gene expression.

The foregoing shows that the delivery system which uses the bubble preparation (TB) with perfluoropropane gas encapsulated therein according to the present invention and the irradiation with low intensity therapeutic ultrasound is expected to be useful in a gene- and nucleic acid-based treatment of cancer.

Example 4. <Production of Bubble Preparation by Shaking>

In Example 1, the gas was emulsified with the homogenizer to prepare the bubble suspension. In Example 4, preparation of a bubble suspension by shaking will be described.

Figure 8:
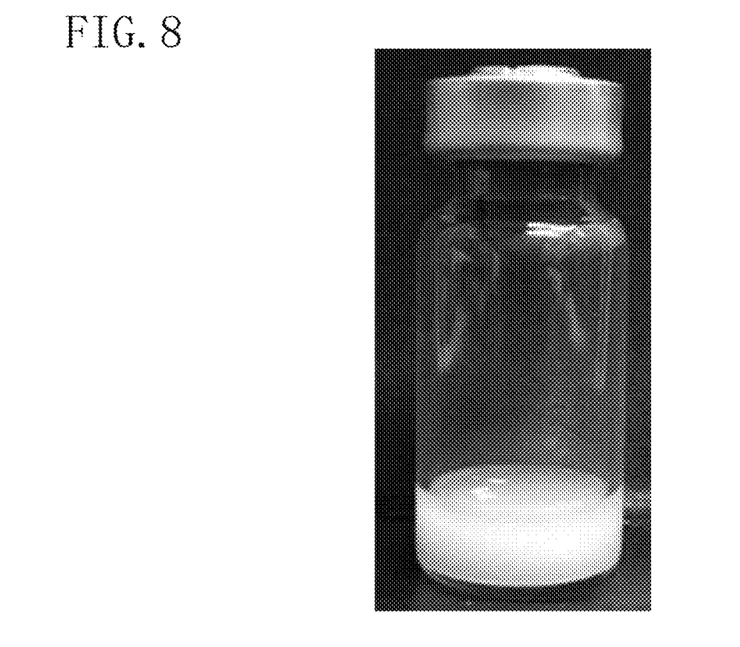
FIG. 8 is a photograph of a bubble preparation produced by shaking.

First, 1 mL of liposomes (with a lipid concentration of 0.5 mM) including DSPC, DSPG, and DSPE-PEG$_{2000}$-OMe at a molar ratio of 30:60:10 was put in a vial, and perfluoropropane gas was substituted for a headspace in the vial. The vial was then ice-cooled. Thereafter, the vial was shaken by a vial shaker for 45 seconds, and ice-cooled again. To remove large bubbles, the vial was left standing upside down for about 15 minutes, and a lower portion of the bubble suspension was collected, as shown in FIG. 8.

Example 5. <Evaluation of Binding Capability of Peptide-Modified Bubbles Prepared with Homogenizer to Target Cell>

As a peptide-modified lipid, DSPE-PEG$_{3400}$ modified with cyclic RGD (cRGD) was prepared. Here, cRGD is a peptide sequence which specifically binds to αVβ3 integrin which over-expresses on the surface of a neovascular endothelial cell of a cancer tissue. Modification of cRGD on the surface of a bubble allows the bubble to function as a targeting bubble which specifically binds to a target cell. An anionic lipid solution including DSPC:DSPG:DSPE-PEG$_{2000}$-OMe:cRGD-modified DSPE-PEG$_{3400}$ at a molar ratio of 30:60:5:5 was brought into contact with perfluoropropane gas (having a gas flowrate of 12 ml/min.), while being agitated in a manner forming a suspension. Thereafter, the gas was emulsified with a homogenizer (at 15000 rpm, for 5 minutes), thereby producing a bubble suspension containing cRGD-modified bubbles. The cRGD modification was at 5 mol. %.

Human umbilical vein endothelial cells (HUVECs) were used as the target cells. The HUVEC is a cell to which cRGD binds.

As a control peptide not binding to the HUVECs, cyclic RAD (cRAD) was used. Bubbles modified with cRAD were prepared in the same manner as the cRGD-modified bubbles. The cRAD modification was at 5 mol. %.

Figure 9:
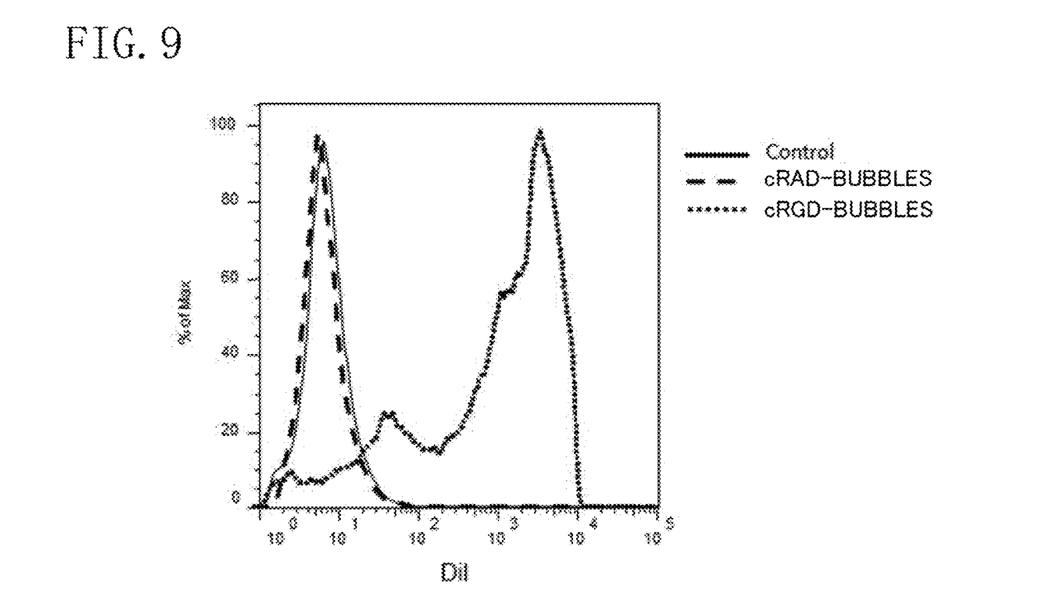
FIG. 9 shows the binding capability of 5 mol. % cRGD-modified bubbles prepared with a homogenizer, to HUVECs.

The cRGD-modified bubbles or cRAD-modified bubbles (DiI label) were added to HUVECs, and the HUVECs were incubated at 37° C. for 10 minutes. Following the incubation, the cells were washed, and the biding of the bubbles to the cells was evaluated using a flow cytometer. As shown in FIG. 9, it has been demonstrated that the bubbles prepared using the homogenizer and modified with 5 mol. % cRGD has greater capability of binding to the HUVECs than the bubbles modified with 5 mol. % cRAD.

Example 6. <Evaluation of Binding Capability of Peptide-Modified Bubbles Prepared by Shaking to Target Cell>

In Example 5, the binding capability of the peptide-modified bubbles prepared with the homogenizer to HUVECs has been described. In Example 6, the binding capability of peptide-modified bubbles prepared by shaking to HUVECs will be described.

As in Example 5, DSPE-PEG$_{3400}$ modified with cyclic RGD (cRGD) was prepared as a peptide-modified lipid. Then, 1 mL of liposomes (with a lipid concentration of 0.5 mM) including DSPC:DSPG:DSPE-PEG$_{2000}$-OMe:cRGD-modified DSPE-PEG$_{3400}$ at a molar ratio of 30:60:5:5 or 30:60:0:10 was put in a respective vial. Perfluoropropane gas was substituted for a headspace in each vial, and the vial was ice-cooled. Thereafter, the vial was shaken by a vial shaker for 45 seconds, and ice-cooled again. To remove large bubbles, each vial was left sanding upside down for about 15 minutes. A lower portion of each bubble suspension was collected, thereby preparing 5 mol. % cRGD-modified bubbles and 10 mol. % cRGD-modified bubbles.

As in Example 5, cyclic RAD (cRAD) was used as the control peptide. cRAD-modified bubbles were prepared by shaking in the same manner as the cRGD-modified bubbles, thereby preparing 5 mol. % cRGD-modified bubbles and 10 mol. % cRGD-modified bubbles.

Figure 10:
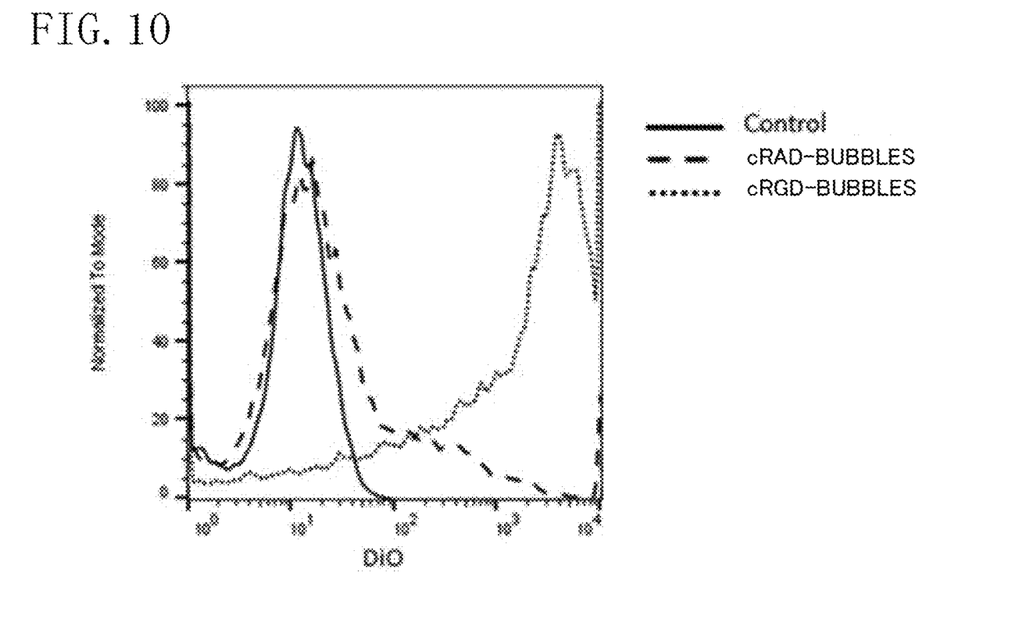
FIG. 10 shows the binding capability of 5 mol. % cRGD-modified bubbles prepared by shaking, to HUVECs.
Figure 11:
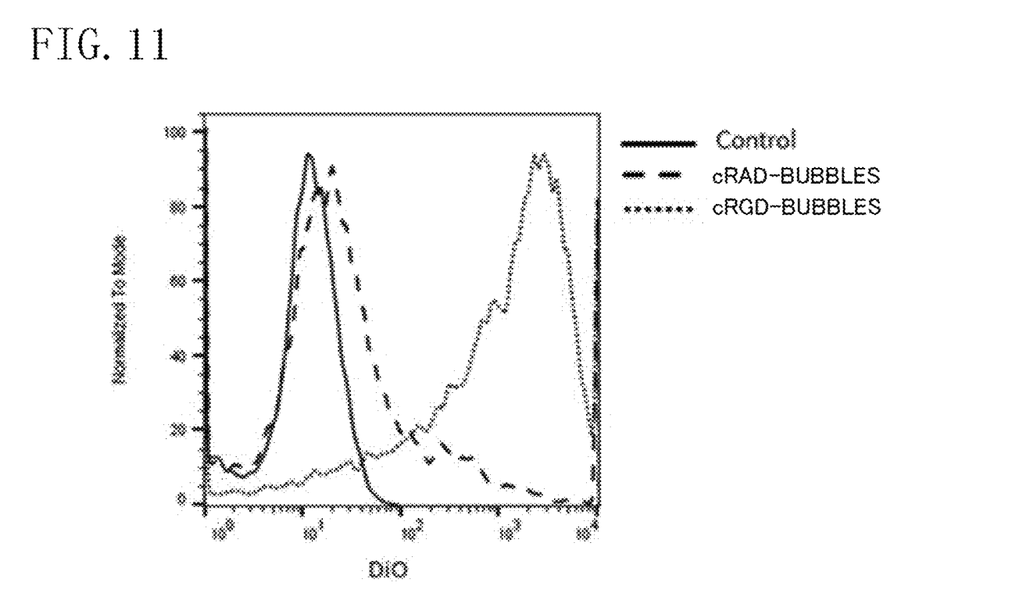
FIG. 11 shows the binding capability of 10 mol. % cRGD-modified bubbles prepared by shaking, to HUVECs.

The cRGD-modified bubbles or cRAD-modified bubbles (DiO label) were added to HUVECs, and the HUVECs were incubated at 37° C. for 30 minutes. Following the incubation, the cells were washed, and the biding of the bubbles to the cells was evaluated using a flow cytometer. As shown in FIG. 10, it has been demonstrated that the bubbles prepared by shaking and modified with 5 mol. % cRGD has greater capability of binding to HUVECs than the bubbles modified with 5 mol. % cRAD. As shown in FIG. 11, it has been demonstrated that the bubbles prepared by shaking and modified with 10 mol. % cRGD has greater capability of binding to HUVECs than the bubbles modified with 10 mol. % cRAD.

Example 7. <Evaluation of Antitumor Effect>

An anionic lipid solution including DSPC:DSPG:DSPE-PEG$_{2000}$-OMe: at a molar ratio of 30:60:10 was brought into contact with perfluoropropane gas (having a gas flowrate of 12 ml/min.), while being agitated in a manner forming a suspension. Thereafter, the gas was emulsified with a homogenizer (at 15000 rpm, for 5 minutes), thereby preparing a bubble suspension. The resultant bubble suspension was freeze-dried to produce a freeze-dried powder. Ultrapure water (2 mL, MilliQ) was added to the freeze-dried powder to suspend the freeze-dried powder in the ultrapure water.

Next, 1×10$^6$ mouse melanoma cells (B16BL6 cells)/50 µm were transplanted to a subcutaneous region of a hinder back of each of C57BL/6j mice. At 7 days after the occurrence of a cancer, 25 μm of the bubbles filtered through a 5 μm filter was administered into the tumor. Immediately after the administration, ultrasound was percutaneously emitted toward the tumor.

Figure 12:
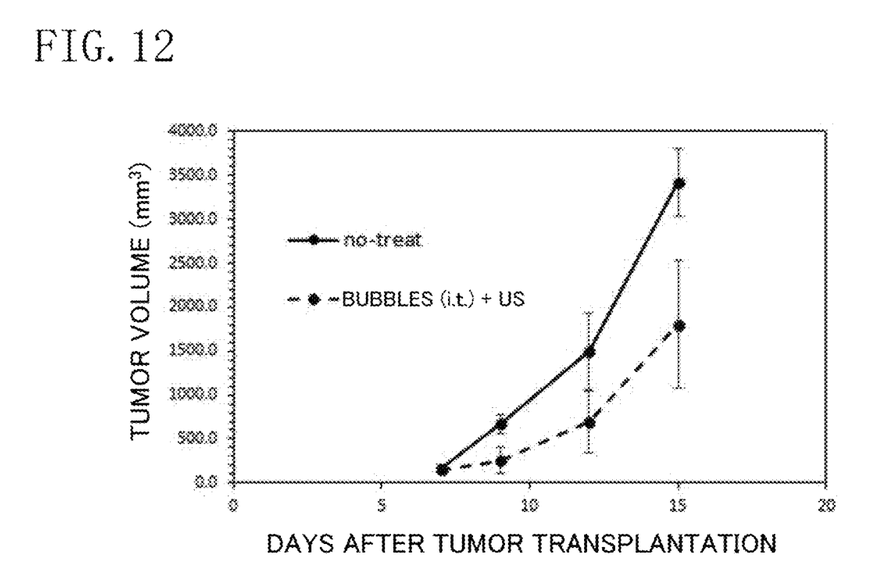
FIG. 12 shows antitumor effect provided by a bubble preparation according to an example.

The ultrasound irradiation conditions were as follows.
Device: sonitron 2000 (Product of Nepa Gene Co., Ltd.)
Frequency: 1 MHz
Intensity: 4 W/cm$^2$
Duty: 50%
Time: 120 secs
Burst Rate: 2 Hz A tumor volume (mm$^3$) was calculated according to the computational expression: (major axis of tumor)×(minor axis of tumor)×(minor axis of tumor)×0.5. The antitumor effect was evaluated using the tumor axes as indexes. As shown in FIG. 12, it has been demonstrated that the bubbles of this example have high antitumor effect.

The present invention is useful for thrombus treatment or cancer treatment.

The invention claimed is:

1. A theranostic bubble preparation comprising:
   bubbles that enable diagnostics and therapeutics of a tissue of interest through an action of diagnostic ultrasound and an action of low intensity therapeutic ultrasound,
   the bubbles each comprising a coating of a lipid and a gas encapsulated in an inner cavity defined by the coating, wherein:
      the lipid forming the coating is an anionic lipid including distearoylphosphatidylcholine (DSPC), distearoylphosphatidylglycerol (DSPG), and 1,2-distearoyl-sn-glycero-3-phosphoethanolamine-N-[methoxy(polyethylene glycol)] (DSPE-PEG) at a molar ratio of 30-36:54-60:10,
      the gas includes at least one of perfluoropropane, perfluorobutane, perfluoropentane, or perfluorohexane, or a mixed gas thereof; and
      the bubbles each have a diameter ranging from 500 nm to 5 μm.

2. The theranostic bubble preparation of claim 1, wherein:
   the lipid forming the coating is an anionic lipid including distearoylphosphatidylcholine (DSPC), distearoylphosphatidylglycerol (DSPG), and 1,2-distearoyl-sn-glycero-3-phosphoethanolamine-N-[methoxy(polyethylene glycol)] (DSPE-PEG) at a weight ratio of 30:60:10, and
   the gas is perfluoropropane.

3. The theranostic bubble preparation of claim 1, wherein the low intensity therapeutic ultrasound has an energy intensity ranging from 0.03 W/cm$^2$ to 50 W/cm$^2$.

4. The theranostic bubble preparation of claim 1, wherein:
   the coating includes DSPC, DSPG, and a DSPE-PEG derivative, and
   the DSPE-PEG derivative is DSPE-PEG-MAL, DSPE-PEG-COOH, DSPE-PEG-NHS, or DSPE-PEG-NH$_2$.

5. The theranostic bubble preparation of claim 4, wherein:
   a ligand is modified on a lipid surface of the coating, and
   the ligand is an arginine-glycine-aspartic acid (RGD) sequence peptide, transferrin, folic acid, hyaluronic acid, galactose, or mannose.

6. A freeze-dried powder produced by freeze-drying a suspension including the theranostic bubble preparation of claim 1 suspended in a carbohydrate solution containing trehalose, inulin, or sucrose.

7. A method comprising the steps of:
   introducing, to a tissue of interest, a suspension which includes water for injection and the theranostic bubble preparation of claim 1 suspended in the water for injection,
   subjecting the tissue of interest to an action of imaging ultrasound having a first frequency to carry out diagnostics based on imaging of the tissue of interest, and
   subjecting the tissue of interest to an action of low intensity ultrasound or low intensity convergent ultrasound having a second frequency to carry out therapeutics for the tissue of interest by a cavitation phenomenon.

8. The method of claim 7, wherein the first frequency ranges from 3.0 MHz to 20 MHz, and the second frequency ranges from 0.5 MHz to 3.0 MHz.

9. The method of claim 7, wherein the tissue of interest is a cancer tissue.

* * * * *